United States Patent
Dobrusskin et al.

(10) Patent No.: US 7,582,877 B2
(45) Date of Patent: Sep. 1, 2009

(54) PORTABLE X-RAY DETECTOR PLATE WITH SHOCK ABSORPTION

(75) Inventors: Christoph Dobrusskin, Eindhoven (NL); Aafje Gijsbertha Koster, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 83 days.

(21) Appl. No.: 11/815,663

(22) PCT Filed: Jan. 27, 2006

(86) PCT No.: PCT/IB2006/050306

§ 371 (c)(1), (2), (4) Date: Aug. 7, 2007

(87) PCT Pub. No.: WO2006/085232

PCT Pub. Date: Aug. 17, 2006

(65) Prior Publication Data

US 2008/0292059 A1    Nov. 27, 2008

(30) Foreign Application Priority Data

Feb. 10, 2005    (EP) .................................. 05100970

(51) Int. Cl.
*H01L 27/00* (2006.01)
(52) U.S. Cl. .................................. 250/370.09
(58) Field of Classification Search . 250/370.1–370.15; 378/167–188, 98.8
See application file for complete search history.

(56) References Cited

U.S. PATENT DOCUMENTS

| | | | | |
|---|---|---|---|---|
| 4,455,671 A | * | 6/1984 | Farrar | 378/170 |
| 4,943,991 A | * | 7/1990 | Mosby | 378/182 |
| 5,370,229 A | | 12/1994 | Kroeckel et al. | |
| 6,533,453 B1 | | 3/2003 | Heidsieck et al. | |
| 6,592,257 B1 | | 7/2003 | Heidsieck et al. | |
| 6,700,126 B2 | | 3/2004 | Watanabe | |
| 2002/0005490 A1 | * | 1/2002 | Watanabe | 250/370.09 |

FOREIGN PATENT DOCUMENTS

| | | |
|---|---|---|
| DE | 3315609 | 10/1984 |
| EP | 933650 | 8/1999 |
| JP | 2002143138 | 5/2002 |
| JP | 2004184679 | 7/2004 |
| JP | 2004219705 | 8/2004 |
| WO | 2004084730 | 10/2004 |

\* cited by examiner

*Primary Examiner*—David P Porta
*Assistant Examiner*—Kiho Kim

(57) ABSTRACT

A portable X-ray detector unit (10) comprising a detection panel (12) housed within a cassette (14), wherein a margin is provided around the detection panel (12), between a peripheral edge thereof and the inner wall of the cassette (14), at at least the corners (16) of the detection panel (12) such that shock absorption functionality may be provided at at least those corners (16), at least one side (18) of the unit (10) having little or no margin so as to maximise the active area of the unit (10) at that side (18) and enable harder-to-reach areas of a subject (200) to be imaged.

9 Claims, 3 Drawing Sheets

PORTABLE X-RAY DETECTOR PLATE WITH SHOCK ABSORPTION

This invention relates generally to a portable X-ray detector plate with shock absorption means for at least minimising the damaging effect of an impact to the detector plate caused, for example, by a fall or knock.

It is widely known, in the field of non-invasive medical diagnosis, to obtain a radiation image of a subject to be imaged with radiation and detecting the intensity distribution of the radiation that has been transmitted through the subject to be imaged. In the following, X-ray systems in particular are referred to. However, it will be appreciated that the present invention can be applied in respect of other types of radiation imaging systems, and the present invention is not necessarily intended to be limited in this regard.

Referring to FIG. 1 of the drawings, there is illustrated schematically a typical X-ray system which comprises an X-ray image detecting sensor unit 3 having a plurality of photoelectric conversion elements. An X-ray source 2, fed by an X-ray generator comprising a high voltage generator 5, generates X-rays that are transmitted through a subject 4 to the sensor unit 3, the photoelectric conversion elements of which generate an image signal representative of the intensity distribution of the radiation transmitted through the subject 4. The image signal is fed to a digital image processing means within a control unit 6 and the resultant image is then displayed.

Portable X-ray systems are known which generally comprise a portable X-ray generating unit and a portable X-ray image detecting sensor unit for use in the case, for example, where a patient (typically in intensive care) is not well enough to be moved to the main X-ray station. However, portable X-ray systems are becoming increasingly more commonly used anyway, because they are relatively very convenient in that the sensor unit can be positioned in any desired orientation relative to the patient to be imaged.

A conventional X-ray image detecting sensor unit, or cassette, comprises an X-ray image detection panel within a substantially rectangular casing. Thus, the sensor unit has an active area that is defined by the size of the detection panel. On the one hand, it is desirable for the edge of the detection panel to be as close as possible to the edge of the casing, so as to maximise the active area, and enable even the harder-to-reach areas of a subject (e.g. under the arm) to be effectively imaged. However, on the other hand, in order to protect the detection panel (and associated electronics) against damage caused by impact to the cassette, it is desirable to have an adequate margin between the detection panel and the inner walls of the cassette so as to enable the provision of adequate shock absorbing means.

Consider, for example, U.S. Pat. No. 6,700,126, which describes a digital X-ray sensor unit in the form of a cassette, wherein shock absorbers made of substantially L-shaped plastic or rubber are disposed at the inner sides of four corners of the casing, between the inner walls of the casing and a support carrying the detection panel, and a margin is provided all the way round the casing between the inner walls thereof and the support periphery to accommodate the shock absorbers. However, because of the margin or gap between the active area and the edge of the cassette, it is difficult to effectively image some areas of a subject, such as under the arm. Referring to FIG. 2 of the drawings, in order to image a spot under the arm of a subject, for example, the subject 200 holds a conventional portable X-ray detector unit 100 in the manner illustrated.

Referring to FIG. 3 of the drawings, the conventional detector unit 100 comprises a detector plate 302 within a casing, wherein a relatively wide margin 304 is provided all the way around the detector plate 302 between a peripheral edge thereof and the casing, and wherein protective shock absorbing elements 306 are provided at least at each corner of the detector plate 302.

However, referring additionally back to FIG. 2 of the drawings, because of the relatively large margin 304 between the upper edge of the active area of the detector plate 302 and the inner wall of the casing 303, there will be an area under the arm that simply cannot be imaged in this manner because the active area of the unit, as defined by the detector plate 302, does not extend all the way to the edge of the unit.

Thus, it is an object of the present invention to provide a portable X-ray detector unit in which the active area of the detection panel is maximised whilst enabling the provision of adequate shock absorbing capability.

In accordance with the present invention, there is provided a portable radiation detector unit, comprising a detection panel housed within a cassette, said detection panel being arranged and configured to receive radiation transmitted through a subject to be imaged and generate an image signal representative of the intensity distribution of said received radiation, wherein a margin for providing shock absorption is provided between the inner wall of said cassette and the peripheral edge of said detection panel at least one corner thereof, with little or no margin being provided along at least a portion of one side thereof.

In a first embodiment, the margin for providing shock absorption is provided between the inner wall of said cassette and the peripheral edge of said detection panel at least one corner thereof and substantially no margin is provided along at least a portion of one side thereof. This may be achieved wherein the shape and configuration of the cassette is such that the edge of the detection panel along said at least one side thereof is substantially immediately adjacent the inner wall of the cassette. Alternatively, the side wall of the cassette may be interrupted along said at least one side of the detection panel, such that at least a portion of said at least one side thereof is exposed.

In another embodiment, a margin may be provided all around the detection panel, between a peripheral edge thereof and the inner wall of the cassette, wherein the width of the margin along at least a portion of one side of the detection panel is less than that at least one corner thereof.

One or more shock absorbing elements may be provided within said margin at at least one corner of said detection panel.

Thus, shock absorption functionality can be selectively provided at one or more of the corners of the detection panel (bearing in mind that, if the unit is dropped, it will generally land on one of its corners), whilst along at least part of one edge, the detection panel (and corresponding active area) is substantially adjacent the inner wall of the cassette, so as to maximise the active area at that part of the unit and enable harder-to-reach parts of the subject (e.g. under the arm) to be effectively imaged.

These and other aspects of the present invention will be apparent from, and elucidated with reference to, the embodiment described herein.

Embodiments of the present invention will now be described by way of examples only and with reference to the accompanying drawings, in which.

In known X-ray detector units, shock absorption means or "buffers" can be provided internally and/or externally of the unit. Thus, if the shock absorption means is provided internally, springs or rubber buffers for example are provided within the margin provided between the detector panel and the inner wall of the cassette or casing surrounding it. If such means are provided externally, it means that the shock absorption means are provided on the outer wall of the cassette or casing. Either or both types of buffering may be provided in a single unit. Equally, either or both types of buffering may be used in the detector unit of the present invention, and the present invention is not necessarily intended to be limited in this regard.

Figure 1:
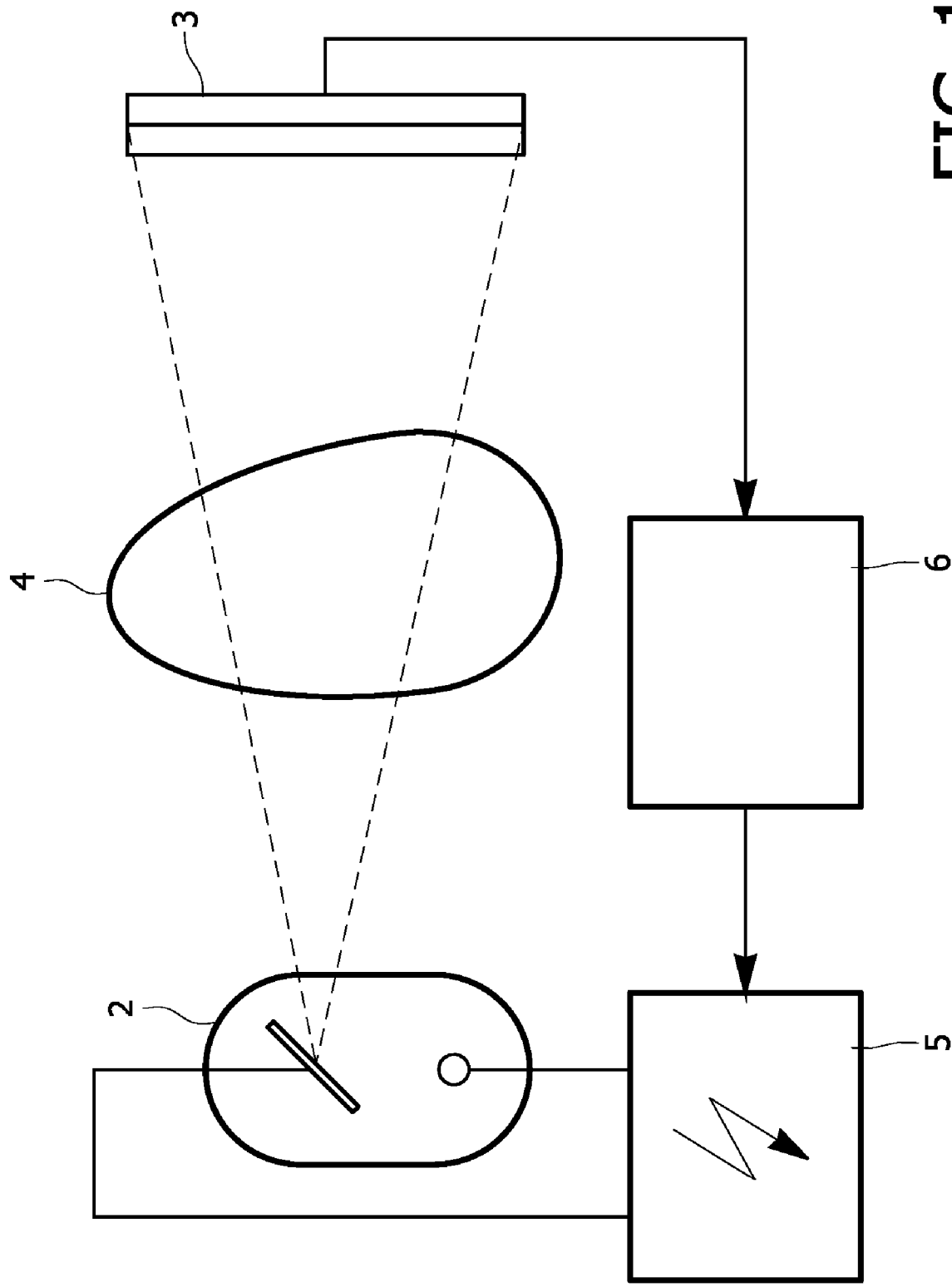
FIG. 1 is a schematic illustration of an X-ray system.
Figure 2:
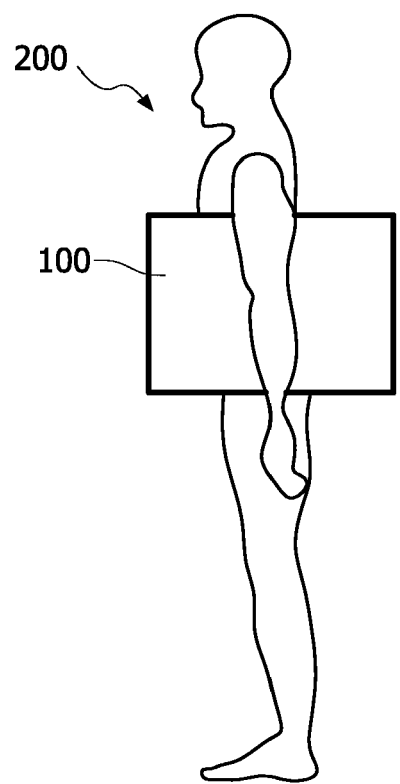
FIG. 2 is a schematic illustration of the manner in which an area under a subject's arm may be imaged using a conventional portable X-ray detector unit.
Figure 3:
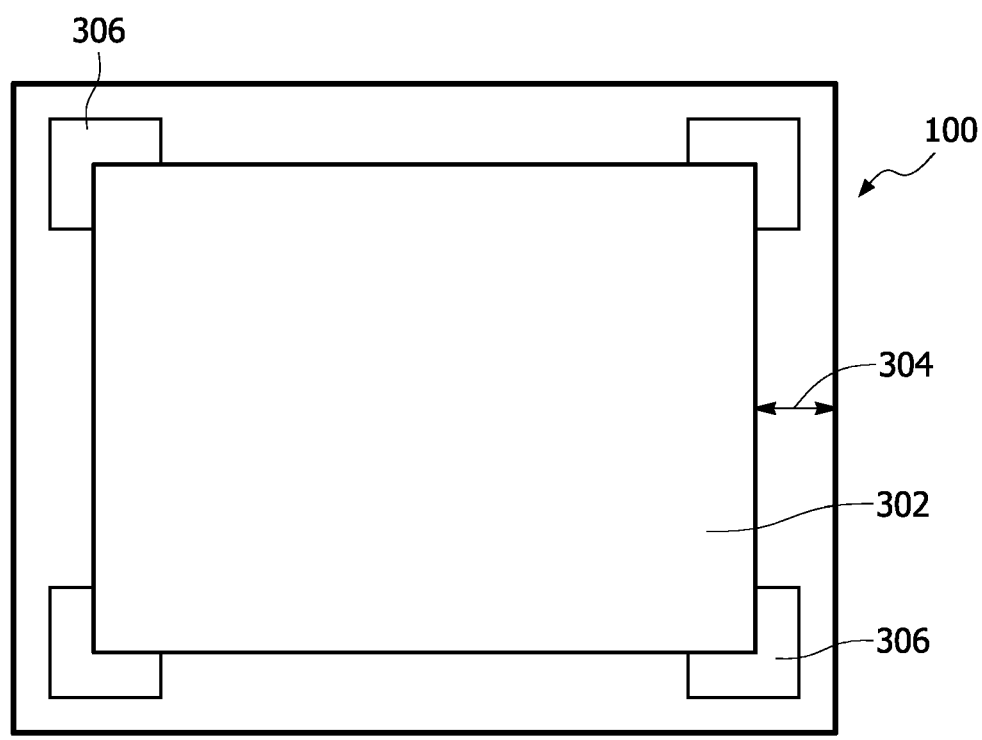
FIG. 3 is a schematic diagram illustrating the configuration of a conventional portable X-ray detector unit.
Figure 4:
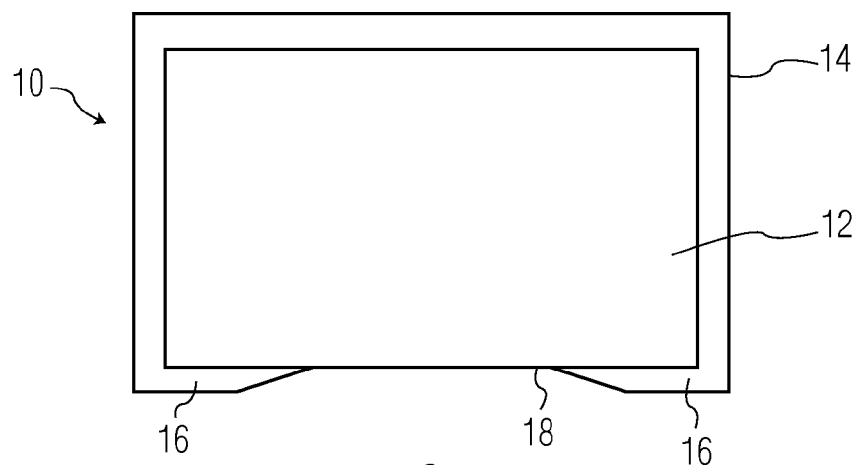
FIG. 4 is a schematic diagram illustrating a portable X-ray detector unit according to a first exemplary embodiment of the present invention.

Thus, referring to FIG. 4 of the drawings, a portable X-ray detector unit 10 according to a first exemplary embodiment of the present invention, comprises a detector plate 12 within a cassette 14. A relatively wide margin is provided between the peripheral edge of the detector plate 12 and the inner wall of the cassette 14 at each of the corners 16 and along three sides of the detector plate 12. However, the cassette 14 along the fourth side 18 of the detector plate 12, spaced from the two respective corners, is shaped and configured so that little or no margin is provided between its peripheral edge and the inner wall of the cassette 14. When such a detector unit 10 falls on the floor, for example, it tends to land on one of its corners. Thus, the relatively wide margin provided at the corners 16 enables shock absorbing functionality at these points to be incorporated (simply by the provision of the margin or by the additional provision of shock absorbing elements (not shown)). Between the corners 16, however, along the sides of the detector plate 12, less protection is required, such that little or no margin can be provided along at least one edge thereof, in between the respective corners 16.

Figure 5:
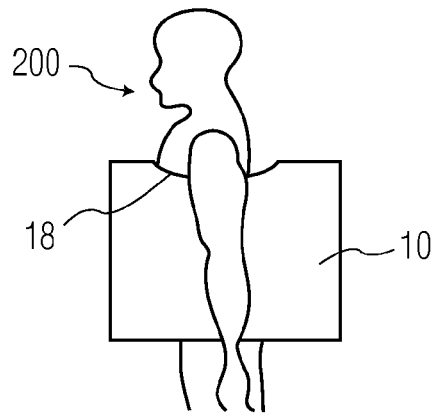
FIG. 5 illustrates schematically how the detector unit of FIG. 4 can be used to effectively image an area under a subject's arm.

Referring to FIG. 5 of the drawings, there is illustrated schematically the detector unit 10 of FIG. 4, when used to image an area under a subject's arm. As before, the detector unit 10 is held by the subject 200, such that the edge 18 of the detector unit 10 having little or no margin between the detector plate and the inner wall of the cassette is located under the patient's arm. In this manner, the active area of the detector unit 10 can be maximised at the desired area.

Figure 6:
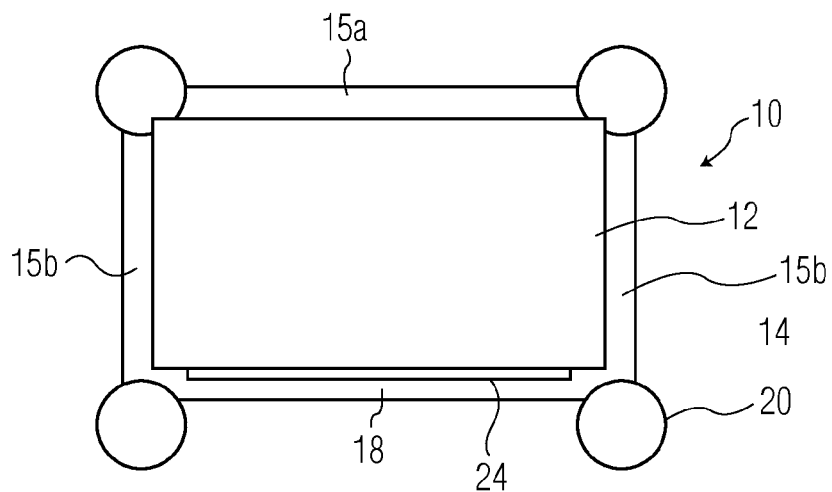
FIG. 6 is a schematic diagram illustrating a portable X-ray detector unit according to a second exemplary embodiment of the present invention.

Referring to FIG. 6 of the drawings, a portable X-ray detector unit 10 according to another exemplary embodiment of the present invention comprises a detector plate 12 housed within a cassette 14, wherein a relatively wide margin 15a is provided between the detector plate 12 and the inner wall of the cassette 14 along one of the longer sides of the unit 10, a relatively narrower margin 15b is provided between the peripheral edge of the detector plate 12 and the inner wall of the cassette 14 along the two shorter sides of the unit 10, and a relatively very narrow margin 18 is provided along the other of the longer sides of the unit 10, wherein shock absorbing elements 20 are provided at each of the corners of the unit 10.

It will be appreciated that the at least one minimal margin can be provided at one or more of the edges of the detector unit, and the or each minimal margin may be protected by, for example, movable, removable and/or flexible (whether movable, removable or otherwise) protective strips of material 24.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A portable radiation detector unit (10), comprising a detection panel (12) housed within a cassette (14), said detection panel (12) being arranged and configured to receive radiation transmitted through a subject (200) to be imaged and generate an image signal representative of the intensity distribution of said received radiation, wherein a margin for providing shock absorption is provided between an inner wall of said cassette and a peripheral edge of said detection panel at at least one corner (16) thereof, with substantially no margin or a reduced margin being provided along at least a portion of one side (18) thereof.

2. A unit (10) according to claim 1, wherein the margin for providing shock absorption is provided between the inner wall of said cassette (14) and the peripheral edge of said detection panel (12) at at least one corner (16) thereof and substantially no margin is provided along at least a portion of one side (18) thereof.

3. A unit (10) according to claim 2, wherein the cassette (14) is configured such that the edge of the detection panel (12) along said at least one side (18) thereof is substantially immediately adjacent the inner wall of the cassette (14).

4. A unit (10) according to claim 2, wherein the side wall of the cassette (14) is interrupted along said at least one side (18) of the detection panel (12), exposing at least a portion of said at least one side thereof.

5. A unit (10) according to claim 1, wherein a margin is provided all around the detection panel (12), between a peripheral edge thereof and the inner wall of the cassette (14), and wherein the width of the margin along at least a portion of one side (18) of the detection panel is less than that at at least one corner (16) thereof.

6. A unit (10) according to claim 1, wherein one or more shock absorbing elements (20) is provided within said margin at at least one corner (16) of said detection panel.

7. A unit (10) according to claim 1, wherein at least said portion along at least one side (18) of said peripheral edge of said detector panel is provided with a protective strip of material.

8. The unit according to claim 7, wherein the protective strip is movable, allowing access to the edge of said detector panel with little or no margin.

9. The unit according to claim 7, wherein the protective strip is removable, allowing access to the edge of said detector panel with little or no margin.

* * * * *